United States Patent
Petschke et al.

(10) Patent No.: US 9,155,515 B2
(45) Date of Patent: Oct. 13, 2015

(54) REGISTRATION OF 4th GENERATION DETECTORS RELATIVE TO THE 3rd GENERATION CT SYSTEM COORDINATES USING 4th GENERATION SINOGRAM DATA

(71) Applicants: Kabushiki Kaisha Toshiba, Minato-ku (JP); Toshiba Medical Systems Corporation, Otawara-shi (JP)

(72) Inventors: Adam Petschke, Lake Bluff, IL (US); Yuexing Zhang, Naperville, IL (US); Yu Zou, Naperville, IL (US)

(73) Assignees: KABUSHIKI KAISHA TOSHIBA, Minato-ku (JP); TOSHIBA MEDICAL SYSTEMS CORPORATION, Otawara-shi (JP)

( * ) Notice: Subject to any disclaimer, the term of this patent is extended or adjusted under 35 U.S.C. 154(b) by 46 days.

(21) Appl. No.: 14/190,829

(22) Filed: Feb. 26, 2014

(65) Prior Publication Data

US 2015/0238161 A1    Aug. 27, 2015

(51) Int. Cl.
*A61B 6/00* (2006.01)
*A61B 6/03* (2006.01)

(52) U.S. Cl.
CPC ............ *A61B 6/547* (2013.01); *A61B 6/035* (2013.01); *A61B 6/4241* (2013.01); *A61B 6/4266* (2013.01)

(58) Field of Classification Search
CPC ...... A61B 6/032; A61B 6/4233; A61B 6/583; A61B 6/4241; A61B 6/482; A61B 6/488; A61B 6/5294; A61B 6/582; A61B 6/4078; A61B 6/4291; A61B 6/5282; A61B 6/547; A61B 6/035; A61B 6/4266; G01N 23/046; G06T 11/005; G01T 1/2907; G01T 7/005; G01T 1/171; H05G 1/02
USPC ............... 378/4, 5, 9, 207; 382/131, 127, 130
See application file for complete search history.

(56) References Cited

U.S. PATENT DOCUMENTS

| | | | |
|---|---|---|---|
| 2013/0336443 A1* | 12/2013 | Gagnon et al. | 378/19 |
| 2014/0233694 A1* | 8/2014 | Wang et al. | 378/5 |
| 2014/0314211 A1* | 10/2014 | Zou et al. | 378/207 |
| 2015/0043796 A1* | 2/2015 | Rigie et al. | 382/131 |
| 2015/0117593 A1* | 4/2015 | Ji et al. | 378/5 |

\* cited by examiner

*Primary Examiner* — Irakli Kiknadze
(74) *Attorney, Agent, or Firm* — Oblon, McClelland, Maier & Neustadt, L.L.P.

(57) ABSTRACT

A method is provided for determining, for a fourth-generation computed tomography (CT) scanner that includes a third-generation X-ray source and detector system and a plurality fixed, sparse photon-counting detectors (PCDs), a position of each PCD of the plurality of PCDs. The method includes determining, for a given PCD, a set of view angles at which the PCD will cast a shadow on the third-generation detector; determining, for each view, by analyzing projection data obtained from a reference scan, a corresponding shadow location on the third-generation detector caused by the given PCD; generating, for each view, a line connecting a position of the X-ray source at the view angle, and a corresponding shadow location of the set of shadow locations; determining locations of all intersection points of the set of lines; and determining a PCD centerline of the given PCD based on the locations of the intersection points.

10 Claims, 7 Drawing Sheets

REGISTRATION OF 4$^{th}$ GENERATION DETECTORS RELATIVE TO THE 3$^{rd}$ GENERATION CT SYSTEM COORDINATES USING 4$^{th}$ GENERATION SINOGRAM DATA

FIELD

Embodiments disclosed herein generally relate to computed tomography (CT) imaging. In particular, embodiments disclosed herein relate to a system and an associated method to register 4$^{th}$-generation detectors relative to 3$^{rd}$-generation CT system coordinates using the shadow pattern of the 4$^{th}$-generation detector.

BACKGROUND

X-ray computed tomography (CT) imaging, in its simplest expression, is an X-ray beam traversing an object and a detector relating the overall attenuation per ray. The attenuation is derived from a comparison of the same ray with and without the presence of the object. From this conceptual definition, several steps are required to properly construct an image. For instance, the finite size of the X-ray generator, the nature and shape of the filter blocking the very low energy X-ray from the generator, the details of the geometry and characteristics of the detector, and the capacity of the acquisition system are all elements that affect how the actual reconstruction is performed.

Figure 1A:
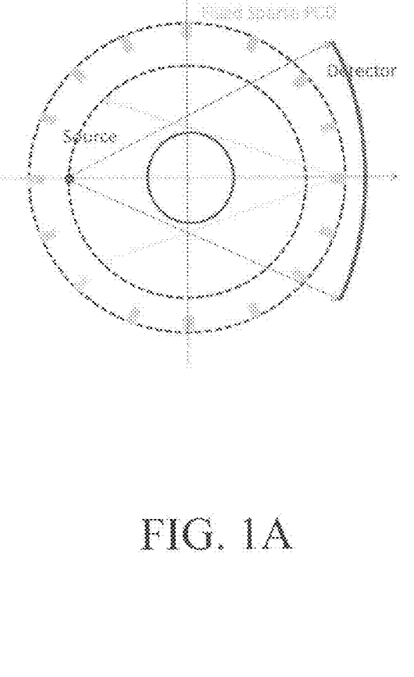
FIGS. 1A and 1B illustrate two 3$^{rd}$/4$^{th}$-generation scanner geometries.
Figure 1B:
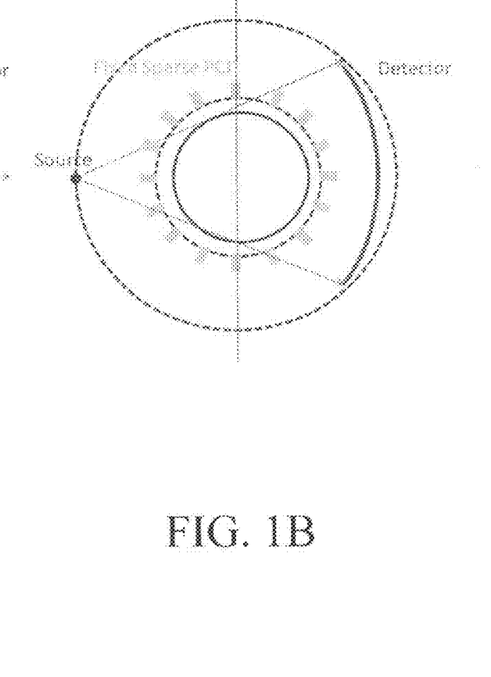

For a combined 3rd- and 4th-generation CT scanner, the system matrix requires knowledge of the offset of the 4$^{th}$-generation sparse photon-counting detectors (PCDs) relative to the 3rd-generation CT system coordinates. For example, FIG. 1A illustrates a "coupled ring" design that includes a third-generation source and detector along with a set of sparse, fixed PCDs arranged in a ring, wherein the source is located inside the ring of PCDs. Alternatively, FIG. 1B illustrates an "inner ring" design that includes a third-generation source and detector along with a set of sparse, fixed PCDs arranged in a ring, wherein the source and detector are located outside the ring of PCDs.

If the offset between the 3$^{rd}$-generation isocenter and the 4$^{th}$-generation detectors is not know precisely, the system matrix will be incorrect, which will cause artifacts in the reconstructed images. Moreover, the offset could change over time due to temperature-induced expansion of materials and gantry rotation.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein.

DETAILED DESCRIPTION

At least two different methods are disclosed for using a fixed object or a plurality of objects between the source and the 3$^{rd}$-generation detector for alignment of the fixed PCD elements with respect to the 3$^{rd}$-generation geometry.

According to one embodiment, there is provided a method for determining, for a fourth-generation computed tomography (CT) scanner that includes a third-generation X-ray source and detector system and a plurality fixed, sparse photon-counting detectors (PCDs), a position of each PCD of the plurality of PCDs, the method comprising: (1) obtaining, for a given PCD of the plurality of PCDs, sinogram data from a reference scan of a plurality of line attenuators arranged at fixed, known positions within the CT scanner; (2) determining, by analyzing the sinogram data, a set of view angles of the X-ray source for which the sinogram data exhibits a decrease in count value, indicating a shadow cast by one of the line attenuators; (3) generating, for each view angle in the set of view angles, a line connecting a position of the X-ray source at the view angle, and a position of a line attenuator, of the plurality of line attenuators, that is closest to the position of the X-ray source at the view angle, to generate a set of lines; (4) extending each line in the set of lines a predetermined distance to generate an extended set of lines; (5) determining locations of all intersection points of the extended set of lines; and (6) determining a PCD centerline of the given PCD based on the determined locations of the intersection points.

In another embodiment, the step of determining the PCD centerline comprises determine the PCD centerline using a least-squares fit of the locations of the intersection points.

In another embodiment, the method further comprises determining a center position of the given PCD by calculating an average of the locations of the intersection points.

According to another embodiment, there is provided an apparatus for determining, for a fourth-generation computed tomography (CT) scanner that includes a third-generation X-ray source and detector system and a plurality fixed, sparse photon-counting detectors (PCDs), a position of each PCD of the plurality of PCDs, the apparatus comprising: a processing circuit configured to obtain, for a given PCD of the plurality of PCDs, sinogram data from a reference scan of a plurality of line attenuators arranged at fixed, known positions within the CT scanner; determine, by analyzing the sinogram data, a set of view angles of the X-ray source for which the sinogram data exhibits a decrease in count value, indicating a shadow cast by one of the line attenuators; generate, for each view angle in the set of view angles, a line connecting a position of the X-ray source at the view angle, and a position of a line attenuator, of the plurality of line attenuators, that is closest to the position of the X-ray source at the view angle, to generate a set of lines; extend each line in the set of lines a predetermined distance to generate an extended set of lines; determine locations of all intersection points of the extended set of lines; and determine a PCD centerline of the given PCD based on the determined locations of the intersection points.

According to another embodiment, there is provided a method for determining, for a fourth-generation computed tomography (CT) scanner that includes a third-generation X-ray source and detector system and a plurality fixed, sparse photon-counting detectors (PCDs), a position of each PCD of the plurality of PCDs, the method comprising: (1) determining, for a given PCD of the plurality of PCDs, a set of view angles at which the PCD will cast a shadow on the third-generation detector; (2) determining, for each view angle in the determined set of view angles, by analyzing projection data obtained from a reference scan, a corresponding shadow location on the third-generation detector caused by the given PCD, to determine a set of shadow locations; (3) generating, for each view angle in the set of view angles, a line connecting a position of the X-ray source at the view angle, and a corresponding shadow location of the set of shadow locations, to generate a set of lines; (4) determining locations of all intersection points of the set of lines; and (5) determining a PCD centerline of the given PCD based on the determined locations of the intersection points.

According to another embodiment, the step of determining the PCD centerline comprises determine the PCD centerline using a least-squares fit of the locations of the intersection points.

According to another embodiment, the method further comprises determining a center position of the given PCD by calculating an average of the locations of the intersection points.

According to another embodiment, there is provided an apparatus for determining, for a fourth-generation computed tomography (CT) scanner that includes a third-generation X-ray source and detector system and a plurality fixed, sparse photon-counting detectors (PCDs), a position of each PCD of the plurality of PCDs, the apparatus comprising: a processing circuit configured to determine, for a given PCD of the plurality of PCDs, a set of view angles at which the PCD will cast a shadow on the third-generation detector; determine, for each view angle in the determined set of view angles, by analyzing projection data obtained from a reference scan, a corresponding shadow location on the third-generation detector caused by the given PCD, to determine a set of shadow locations; generate, for each view angle in the set of view angles, a line connecting a position of the X-ray source at the view angle, and a corresponding shadow location of the set of shadow locations, to generate a set of lines; determine locations of all intersection points of the set of lines; and determine a PCD centerline of the given PCD based on the determined locations of the intersection points.

Figure 2:
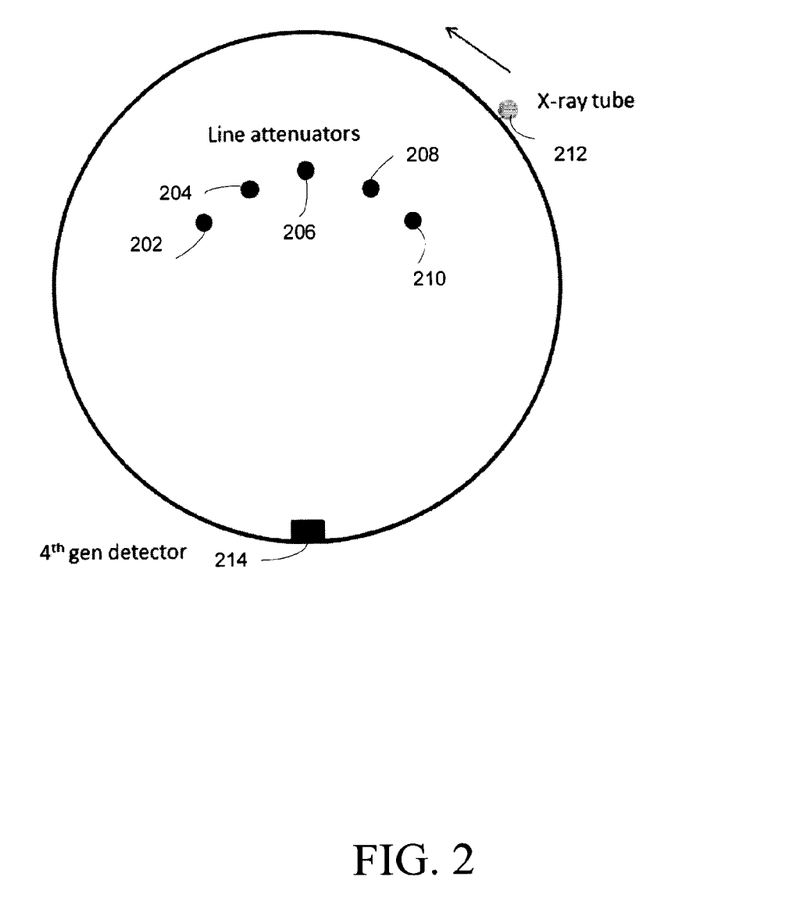
FIG. 2 illustrates a CT scanner geometry in a first embodiment.

Referring now to the drawings, wherein like reference numerals designate identical or corresponding parts throughout the several views, FIG. 2 illustrates one embodiment for alignment of the $4^{th}$-generation detector elements.

In FIG. 2, highly attenuating line objects, e.g., objects 202-210, are inserted in the field of view between the source and the PCDs for a registration scan. Although five line attenuator objects are shown in FIG. 2, any number of line attenuators can be used. In this embodiment, the exact positions of the line objects 202-210 can be determined using images reconstructed from projection data obtained by the $3^{rd}$-generation detector. Moreover, the exact position of the X-ray source is known for each view angle.

Figure 3:
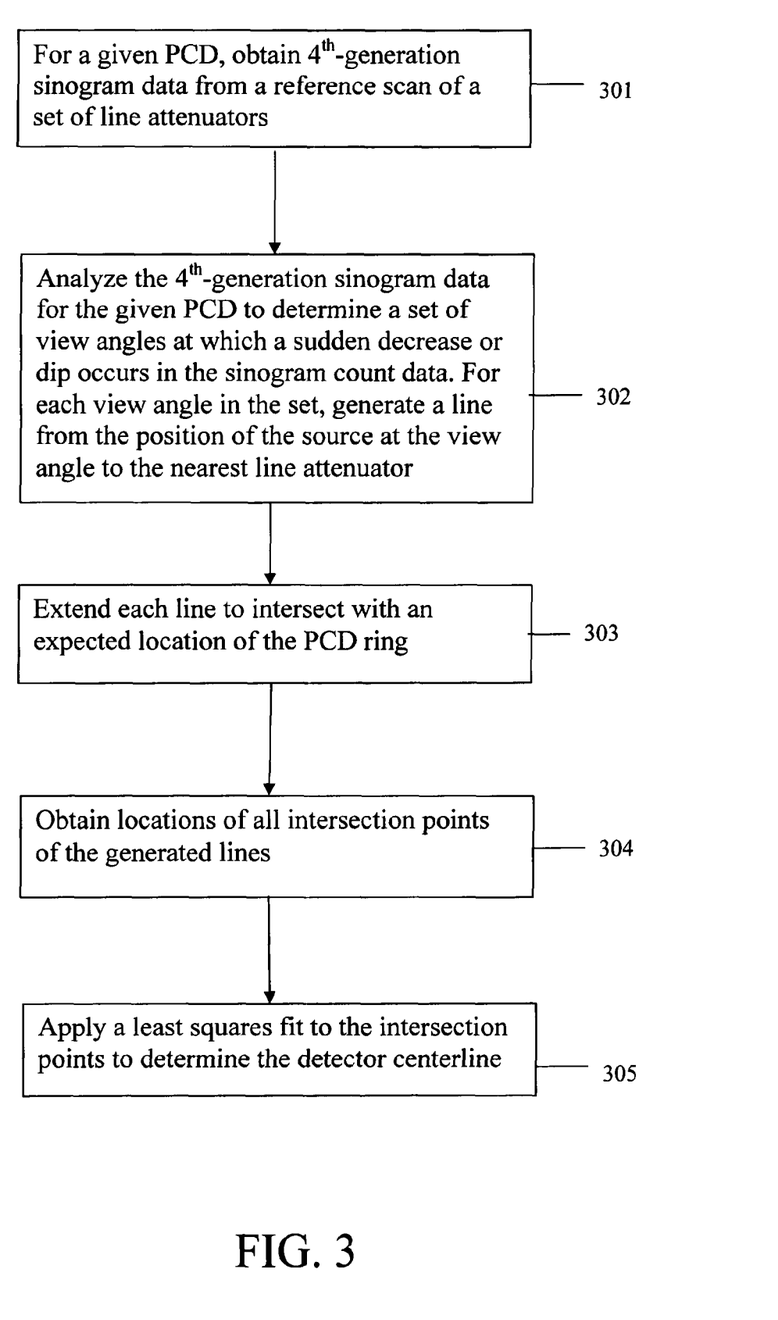
FIG. 3 is a flowchart illustrating a first method of determining a PCD location.

FIG. 3 is a flowchart illustrating a method of determining the position of a PCD using a set of line attenuators, as shown in FIG. 2.

In step 301, for a given PCD, the $4^{th}$-generation sinogram data is obtained from the reference scan of the line attenuators. The sinogram data, e.g., the total counts for the detector as a function of view angle will show a sudden decrease or "dip" that corresponds to one of the line attenuators 202-210 being directly in line between the source and the given PCD.

In step 302, for each dip in the $4^{th}$-generation sinogram data, a line is generated between the location of the X-ray source (view angle corresponding to the dip) and the closest one of the line attenuators. The coordinates of each line attenuator is known and the location of the X-ray source is known. Thus, the distance from the X-ray source to each line attenuator can be determined using the distance formula and the closest line attenuator can be determined as that having the smallest calculated distance. Accordingly, the coordinates of the closest line attenuator and the coordinates of the X-ray source are used to define the line in this step.

Figure 4:
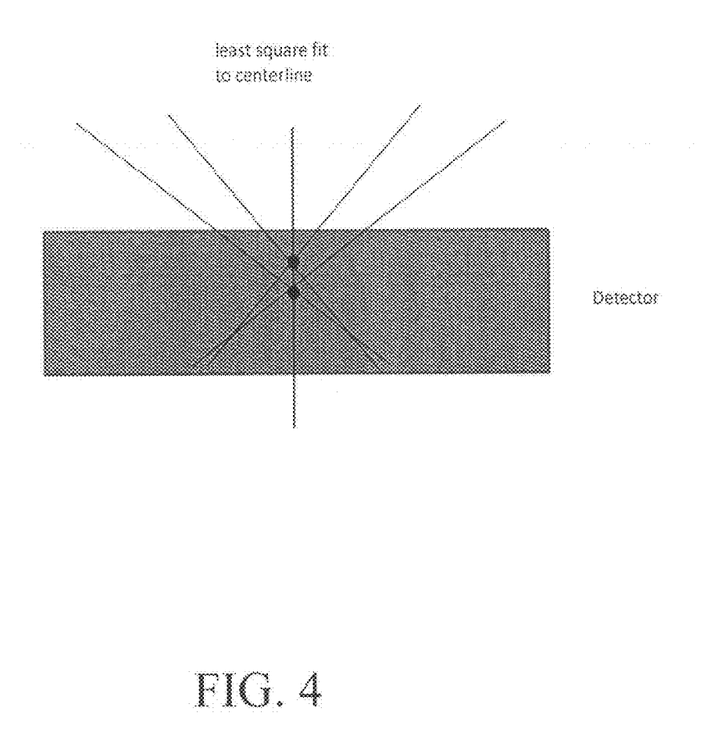
FIG. 4 illustrates a first method of determining a PCD location.

In step 303, each line is extended a predetermined distance to ensure intersection with the approximate location of the PCD ring. For example, FIG. 4 illustrates lines generated for a given PCD and the line attenuator objects shown in FIG. 2. Note that the lines may not meet at a single point due to measurement errors and the size, shape, depth of interaction, and polar effects in the detectors. However, lines drawn through attenuator objects that are located on opposite sides of the detector centerline for the given PCD will intersect somewhere on the detector centerline, as shown in FIG. 4.

In step 304, the locations of all of the intersection points are obtained. Note that the intersection points will form an approximate line on the PCD centerline, perpendicular to PCD surface.

In step 305, a least squares fit of the intersection points is used to determine the detector centerline. Other line-fitting methods can be used to find the centerline of the given PCD. Alternatively, the locations of the intersection points can be averaged to determine an (x,y) location of the PCD.

Note that steps 301-305 are repeated for each PCD in the fixed PCD ring to obtain the corresponding detector centerline or the (x,y) location of the PCD.

Figure 5:
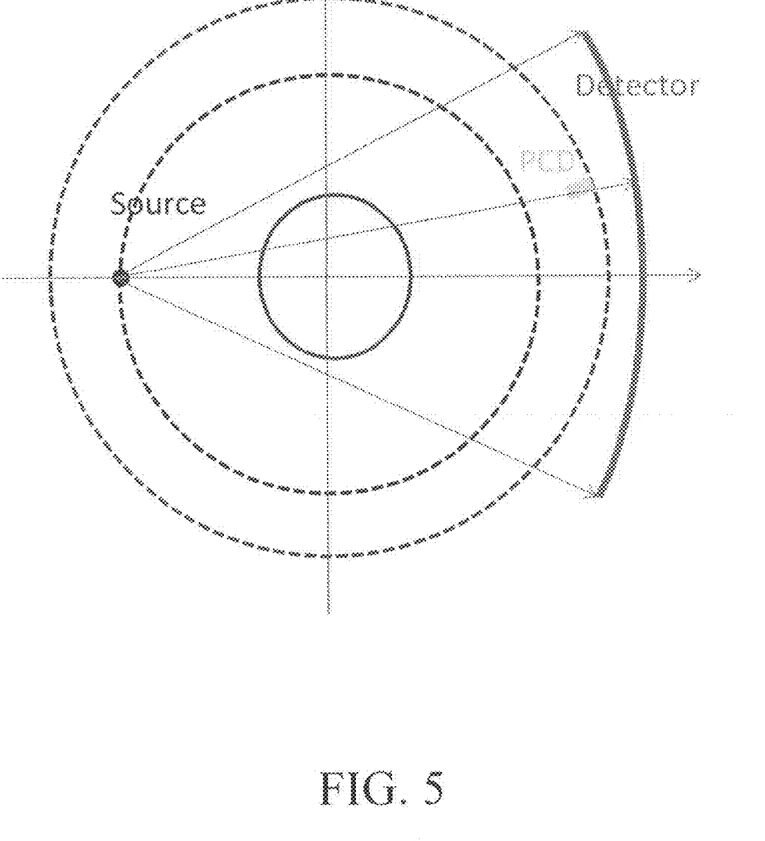
FIG. 5 illustrates a CT scanner geometry in a second embodiment.
Figure 6:
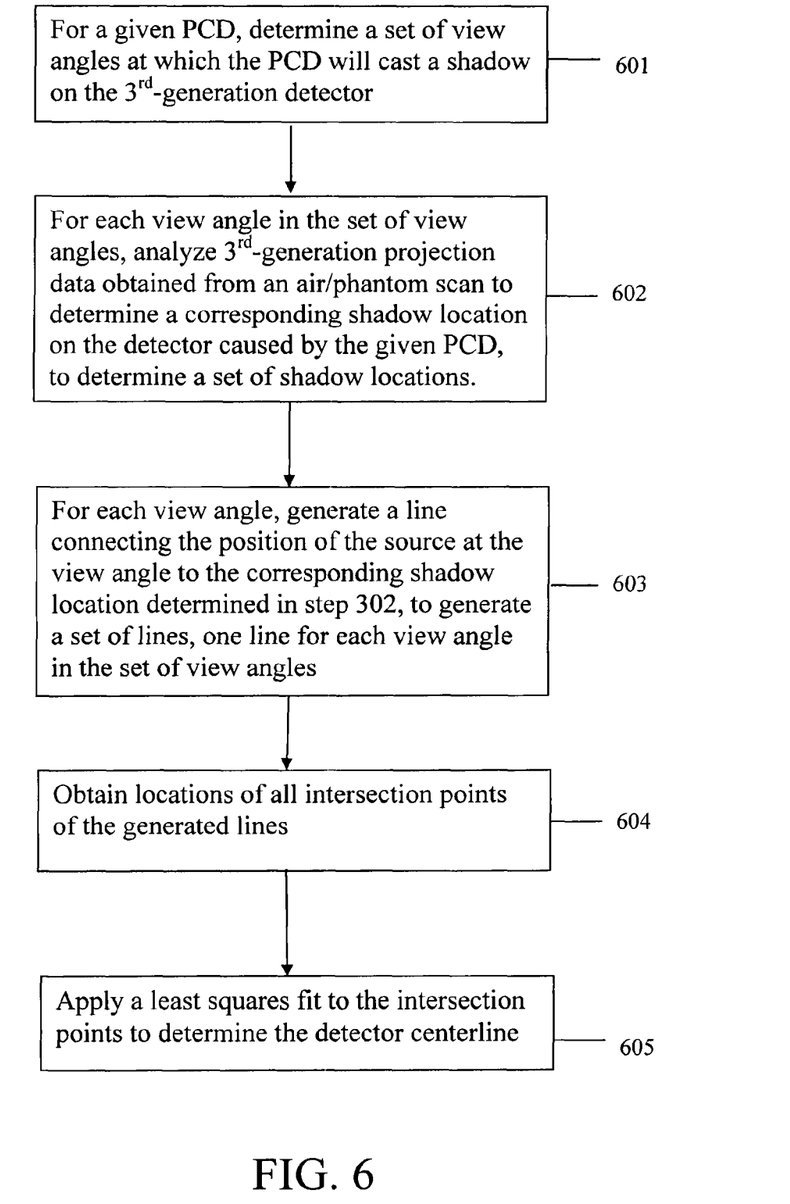
FIG. 6 is a flowchart illustrating a second method of determining a PCD location.

Another embodiment of the present disclosure is illustrated in FIGS. 5 and 6. In the scanner geometry of FIG. 5, at a given view angle, the illustrated PCD will cast a "shadow" in the data collected by the $3^{rd}$-generation detector. Thus, the shadow position on the $3^{rd}$-generation detector can be determined for the given view angle and a straight line can be established between the shadow position and the position of the source at the given view angle. This straight line will pass through the given PCD. Further, a straight line can be obtained for several different view angles for the given PCD, and the thus-obtained straight lines will intersect, establishing the location of the given PCD. The centerline of the PCD can be determined using a least-squares fit to the line intersection points. Alternatively, the line intersection points can be averaged to find an (x,y) location of the given PCD. This method can be repeated for each of the PCDs in the scanner system.

A flowchart of this embodiment is illustrated in FIG. 6. Note that the steps in FIG. 6 apply to a given PCD, but are repeated for all of the PCDs in the CT scanner system.

In step 601, for a given PCD, a set of view angles at which the given PCD will cast a shadow on the 3rd-generation detector is determined from the geometry of the scanner system and the approximate location of the PCD.

In step 602, for each view angle in the set of view angles determined in step 601, 3rd-generation projection data obtained from an air/phantom scan is analyzed to determine a corresponding shadow location on the detector caused by the given PCD so as to determine a set of shadow locations. Note that there will be one shadow location on the $3^{rd}$-generation detector for the given PCD at a given view angle.

In step 603, for each view angle, a line is generated connecting the position of the source at the view angle to the corresponding shadow location (of the set of shadow locations) determined in step 302, to generate a set of lines, one line for each view angle in the set of view angles.

In step 604, the locations of all of the intersection points are obtained. Note that the intersection points will form an approximate line on the PCD centerline, perpendicular to PCD surface.

In step 605, a least squares fit of the intersection points is used to determine the detector centerline. Other line-fitting methods can be used to find the centerline of the given PCD. Alternatively, the locations of the intersection points can be averaged to determine an (x,y) location of the PCD.

Note that steps 601-605 are repeated for each PCD in the fixed PCD ring to obtain the corresponding detector centerline or the (x,y) location of the PCD.

Figure 7:
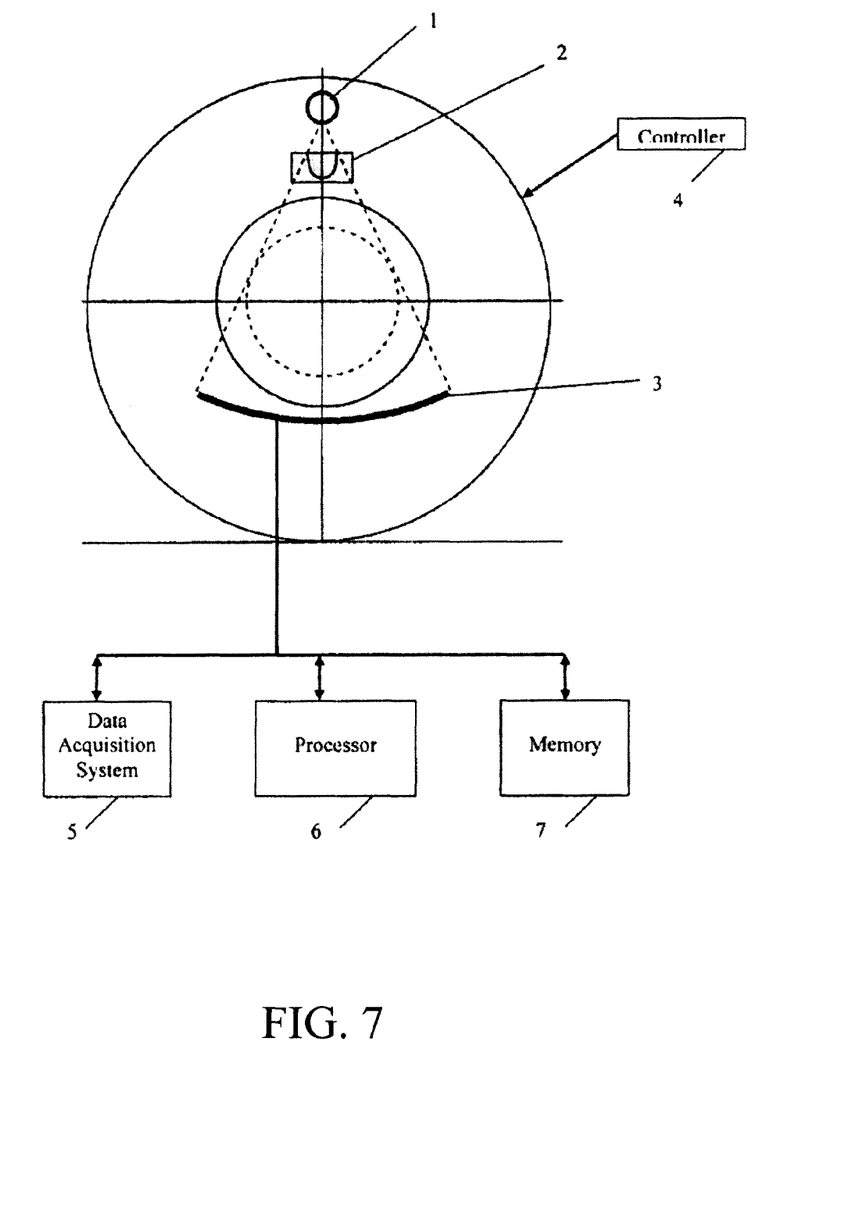
FIG. 7 illustrates a CT scanner system according to the present embodiments.

FIG. 7 illustrates the basic structure of a CT scanner apparatus that includes the detectors described herein. The CT apparatus of FIG. 7 includes an X-ray tube 1, filters and collimators 2, and detector 3. As shown in FIGS. 1A, 1B, and 5, the CT apparatus also includes sparse, fixed energy-discriminating detectors, creating a $4^{th}$-generation scanner. The CT apparatus will also include additional mechanical and electrical components such as a gantry motor and a controller 4 to control the rotation of the gantry, control the X-ray source, and control a patient bed. The CT apparatus also includes a data acquisition system 5 and a processor 6 to generate CT images based on the projection (view) data acquired by the data acquisition system. The processor 6 can be a CPU or other hardware processing circuit that can execute a computer program. The processor and data acquisition system make use of a memory 7, which is configured to store, e.g., projection data obtained from the detector and reconstructed images.

In one embodiment, the processor is configured/programmed to perform the steps set forth in the flowcharts of FIGS. 3 and 6.

In one embodiment, the $4^{th}$-generation spectral computed tomography (CT) scanner apparatus shown in FIGS. 1A, 1B, and 7 includes a rotating X-ray source 1, a $3^{rd}$-generation detector 3, and a plurality of fixed, energy-discriminating detectors (FIGS. 1A, 1B). Further, the hardware processor (processing circuit) 6 is configured to execute a program that causes the processing circuit to (1) obtain, for a given PCD of the plurality of PCDs, sinogram data from a reference scan of a plurality of line attenuators arranged at fixed, known positions within the CT scanner; (2) determine, by analyzing the sinogram data, a set of view angles of the X-ray source for which the sinogram data exhibits a decrease in count value, indicating a shadow cast by one of the line attenuators; (3) generate, for each view angle in the set of view angles, a line connecting a position of the X-ray source at the view angle, and a position of a line attenuator, of the plurality of line attenuators, that is closest to the position of the X-ray source at the view angle, to generate a set of lines; (4) extend each line in the set of lines a predetermined distance to generate an extended set of lines; (5) determine locations of all intersection points of the extended set of lines; and (6) determine a PCD centerline of the given PCD based on the determined locations of the intersection points.

Further, the hardware processor (processing circuit) 6 is configured to execute a program that causes the processing circuit to (1) determine, for a given PCD of the plurality of PCDs, a set of view angles at which the PCD will cast a shadow on the third-generation detector; (2) determine, for each view angle in the determined set of view angles, by analyzing projection data obtained from a reference scan, a corresponding shadow location on the third-generation detector caused by the given PCD, to determine a set of shadow locations; (3) generate, for each view angle in the set of view angles, a line connecting a position of the X-ray source at the view angle, and a corresponding shadow location of the set of shadow locations, to generate a set of lines; (4) determine locations of all intersection points of the set of lines; and (5) determine a PCD centerline of the given PCD based on the determined locations of the intersection points.

As one of ordinary skill in the art would recognize, the processor 6 can include a CPU that can be implemented as discrete logic gates, as an Application Specific Integrated Circuit (ASIC), a Field Programmable Gate Array (FPGA) or other Complex Programmable Logic Device (CPLD). An FPGA or CPLD implementation may be coded in VHDL, Verilog, or any other hardware description language and the code may be stored in an electronic memory directly within the FPGA or CPLD, or as a separate electronic memory. Further, the memory may be non-volatile, such as ROM, EPROM, EEPROM or FLASH memory. The memory can also be volatile, such as static or dynamic RAM, and a processor, such as a microcontroller or microprocessor, may be provided to manage the electronic memory as well as the interaction between the FPGA or CPLD and the memory.

Alternatively, the CPU in the processor 6 can execute a computer program including a set of computer-readable instructions that perform the functions described herein, the program being stored in any of the above-described non-transitory electronic memories and/or a hard disk drive, CD, DVD, FLASH drive or any other known storage media. Further, the computer-readable instructions may be provided as a utility application, background daemon, or component of an operating system, or combination thereof, executing in conjunction with a processor, such as a Xenon processor from Intel of America or an Opteron processor from AMD of America and an operating system, such as Microsoft VISTA, UNIX, Solaris, LINUX, Apple, MAC-OS and other operating systems known to those skilled in the art.

Once processed by a pre-reconstruction processor, the processed signals are passed to a reconstruction processor, which is configured to generate CT images. The images are stored in the memory, and/or displayed on a display. As one of ordinary skill in the art would recognize, memory can be a hard disk drive, CD-ROM drive, DVD drive, FLASH drive, RAM, ROM or any other electronic storage known in the art. The display can be implemented as an LCD display, CRT display, plasma display, OLED, LED or any other display known in the art. As such, the descriptions of the memory and the display provided herein are merely exemplary and in no way limit the scope of the present advancements.

While certain embodiments have been described, these embodiments have been presented by way of example only, and are not intended to limit the scope of the inventions. Indeed the novel methods and systems described herein may be embodied in a variety of other forms; furthermore, various omissions, substitutions, and changes in the form of the methods and systems described herein may be made without departing from the spirit of the inventions. The accompanying claims and their equivalents are intended to cover such forms or modifications as would fall within the scope and spirit of the inventions.

The invention claimed is:

1. A method for determining, for a fourth-generation computed tomography (CT) scanner that includes a third-generation X-ray source and detector system and a plurality fixed, sparse photon-counting detectors (PCDs), a position of each PCD of the plurality of PCDs, the method comprising:

obtaining, for a given PCD of the plurality of PCDs, sinogram data from a reference scan of a plurality of line attenuators arranged at fixed, known positions within the CT scanner;

determining, by analyzing the sinogram data, a set of view angles of the X-ray source for which the sinogram data exhibits a decrease in count value, indicating a shadow cast by one of the line attenuators;

generating, for each view angle in the set of view angles, a line connecting a position of the X-ray source at the view angle, and a position of a line attenuator, of the plurality of line attenuators, that is closest to the position of the X-ray source at the view angle, to generate a set of lines;

extending each line in the set of lines a predetermined distance to generate an extended set of lines;

determining locations of all intersection points of the extended set of lines; and determining a PCD centerline of the given PCD based on the determined locations of the intersection points.

2. The method of claim 1, wherein the step of determining the PCD centerline comprises determine the PCD centerline using a least-squares fit of the locations of the intersection points.

3. The method of claim 1, further comprising:
determining a center position of the given PCD by calculating an average of the locations of the intersection points.

4. The method of claim 1, further comprising:
repeating the obtaining, determining, generating, extending, determining, and determining steps of claim 1 for each PCD in the plurality of PCDs.

5. An apparatus for determining, for a fourth-generation computed tomography (CT) scanner that includes a third-generation X-ray source and detector system and a plurality fixed, sparse photon-counting detectors (PCDs), a position of each PCD of the plurality of PCDs, the apparatus comprising:
a processing circuit configured to
obtain, for a given PCD of the plurality of PCDs, sinogram data from a reference scan of a plurality of line attenuators arranged at fixed, known positions within the CT scanner;

determine, by analyzing the sinogram data, a set of view angles of the X-ray source for which the sinogram data exhibits a decrease in count value, indicating a shadow cast by one of the line attenuators;

generate, for each view angle in the set of view angles, a line connecting a position of the X-ray source at the view angle, and a position of a line attenuator, of the plurality of line attenuators, that is closest to the position of the X-ray source at the view angle, to generate a set of lines;

extend each line in the set of lines a predetermined distance to generate an extended set of lines;

determine locations of all intersection points of the extended set of lines; and determine a PCD centerline of the given PCD based on the determined locations of the intersection points.

6. A method for determining, for a fourth-generation computed tomography (CT) scanner that includes a third-generation X-ray source and detector system and a plurality fixed, sparse photon-counting detectors (PCDs), a position of each PCD of the plurality of PCDs, the method comprising:
determining, for a given PCD of the plurality of PCDs, a set of view angles at which the PCD will cast a shadow on the third-generation detector;

determining, for each view angle in the determined set of view angles, by analyzing projection data obtained from a reference scan, a corresponding shadow location on the third-generation detector caused by the given PCD, to determine a set of shadow locations;

generating, for each view angle in the set of view angles, a line connecting a position of the X-ray source at the view angle, and a corresponding shadow location of the set of shadow locations, to generate a set of lines;

determining locations of all intersection points of the set of lines; and determining a PCD centerline of the given PCD based on the determined locations of the intersection points.

7. The method of claim 6, wherein the step of determining the PCD centerline comprises determine the PCD centerline using a least-squares fit of the locations of the intersection points.

8. The method of claim 6, further comprising:
determining a center position of the given PCD by calculating an average of the locations of the intersection points.

9. The method of claim 6, further comprising:
repeating the determining, determining, generating, determining, and determining steps of claim 6 for each PCD in the plurality of PCDs.

10. An apparatus for determining, for a fourth-generation computed tomography (CT) scanner that includes a third-generation X-ray source and detector system and a plurality fixed, sparse photon-counting detectors (PCDs), a position of each PCD of the plurality of PCDs, the apparatus comprising:
a processing circuit configured to
determine, for a given PCD of the plurality of PCDs, a set of view angles at which the PCD will cast a shadow on the third-generation detector;

determine, for each view angle in the determined set of view angles, by analyzing projection data obtained from a reference scan, a corresponding shadow location on the third-generation detector caused by the given PCD, to determine a set of shadow locations;

generate, for each view angle in the set of view angles, a line connecting a position of the X-ray source at the view angle, and a corresponding shadow location of the set of shadow locations, to generate a set of lines;

determine locations of all intersection points of the set of lines; and determine a PCD centerline of the given PCD based on the determined locations of the intersection points.

* * * * *